United States Patent [19]

Takayama et al.

[11] 4,344,888
[45] Aug. 17, 1982

[54] 24,25-DIHYDROXYCHOLESTANS AND PROCESS FOR PREPARING THE SAME

[75] Inventors: Hiroaki Takayama, Tokyo; Sachiko Yamada, Hachioji; Masayuki Ohmori, Kanagawa, all of Japan

[73] Assignee: Chugai Seiyaku Kabushiki Kaisha, Tokyo, Japan

[21] Appl. No.: 287,052

[22] Filed: Jul. 27, 1981

[30] Foreign Application Priority Data

Aug. 5, 1980 [JP] Japan ................. 55-106774

[51] Int. Cl.³ ............................................ C07J 17/00
[52] U.S. Cl. ..................... 260/397.2; 260/239.55 D; 260/239.5
[58] Field of Search ................... 260/397.2, 239.55 D

[56] References Cited

U.S. PATENT DOCUMENTS 4,028,349  6/1977  Partridge et al. .......... 260/239.55 D
4,204,995  5/1980  Barner et al. .................... 260/397.2

OTHER PUBLICATIONS

Seki, M., et al. "Synthesis of Active Forms of Vitamin D VI[1] Synthesis of (24R)-and (24S)-24,25-Dihydrpxyvitamin D₃", *Tetrahedron Letters*, No. 1, pp. 15–18, 1975.

Isheguro, M., et al. "Studies on Steroids. LI. Stereoselective Introduction of 22-and 24-Hydroxyl Function in the Steroidal Side Chain", *Chem. Pharm. Bull.*, 26 (12) 3715-3721 (1978).

Lam, H. Y., et al. "24,25-Dihydrovitamin D₃. Synthesis and Biological Activity", *Biochemistry*, vol. 12, No. 24, 4851-4855 (1973).

*Primary Examiner*—Elbert L. Roberts
*Attorney, Agent, or Firm*—Browdy and Neimark

[57] ABSTRACT

A 24,25-dihydroxycholestane derivatives of the formula

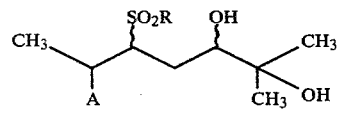

wherein A is a steroid residue and R is an aryl group and a process for preparation of the same are disclosed. The derivatives are an intermediate for synthesis of 24,25-dihydroxycholecalciferol having useful physiological activity like that of vitamin D₃. 24,25-Dihydroxycholecalciferol can be produced in an industrially advantageous method via the intermediate which is easily prepared from commercially available starting compounds.

8 Claims, No Drawings

24,25-DIHYDROXYCHOLESTANS AND PROCESS FOR PREPARING THE SAME

This invention relates to an intermediate for synthesis of 24,25-dihydroxycholecalciferol having potential use as medicines and a process for preparing the same.

24,25-Dihydroxycholecalciferol is a metabolite of vitamin $D_3$, and is known to have physiological activity like that of vitamin D. The metabolite 24,25-dihydroxycholecalciferol is a (24R)-form and, as is well known, its physiological activity differs from that of a (24S)-isomer not found in the metabolite. These isomers have been comparatively easy to produce in the form of a mixture, but no process for separation of each isomer has been found on an industrial scale. This has been one great obstacle to the commercial supply of the compound as a medicine. A mixture of each isomer: 24ξ,25-dihydroxycholecalciferol [(24ξ)-form], [(24R)-form and (24S)-form], can be prepared by various known methods using various intermediate as follows. 24ξ,25-Dihydroxycholesterol is prepared from desmosterol acetate (as in Japanese Patent Public Disclosure No. 109367/74); 24ξ,25-dihydroxycholecalciferol is prepared from 3β-acetoxy-27-nor-5-cholesten-25-one [as in Biochemistry, 12, 4851 (1973)], 24ξ,25-dihydroxycholecalciferol is prepared from desmosterol acetate [as in Compt. rend. Acad. Sci. (Paris), 278, 529 (1974)] and 3β,24ξ,25-trihydroxycholest-5,7-diene is prepared from ergosterol. None of these methods are sterospecific, and the products are diastereomeric mixtures at 24-position, since isolation of the desired 24-isomer from these compounds is very difficult on an industrial scale. Two stereospecific methods are known to produce 24,25-dihydroxycholecalciferol: one is to isolate 24ξ,25-dihydrocholesterol into (24R)- and (24S)-isomers, i.e. 24R,25- and 24S,25-dihydroxycholesterol to thereby obtain the corresponding 24R,25- and 24S,25- dihydroxycholecalciferols [as in Tetrahedron Letters, 15 (1975)], and the other is to produce 24R,25- and 24S,25-dihydroxycholecalciferols from steroid derivatives having given stereospecificity at 24-position (as in Japanese Patent Public Disclosure No. 108960/77). But both methods require complex means for isolation of the desired diastereomeric isomers at 24-position and hence are not suitable for use on an industrial scale.

To solve these problems, we have made various studies on the stereospecific and industrially advantageous synthetic procedure for the preparation of 24,25-dihydroxycholecalciferol and have found out an effective method of synthesis of intermediate as follows. 24R,25- and 24S,25-dihydroxycholestane derivative can be prepared by reacting 22-arylsulfonyl derivative of the formula (I) with an optically active 3-methyl-1,2,3-butanetriol derivative of the formula (II) derived from optically active glyceric acid, and then by removing the aryl sulfonyl group at 22-position.

This invention relates to a process for producing a 24,25-dihydroxycholestane derivative of the formula (III):

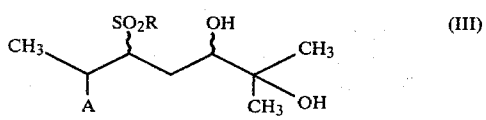

(wherein A is a steroid residue, preferably a steroid residue having a steroid skelton containing a methyl group at each of 10- and 13-positions, and R is an aryl group, preferably a phenyl group, an alkyl ($C_1$-$C_2$) substituted phenyl group or a phenyl-substituted phenyl group) by reacting a compound of the formula (I):

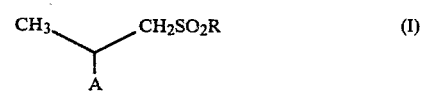

(wherein A and R are the same as defined above) with a compound of the formula (II):

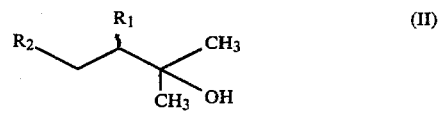

[wherein $R_1$ is a hydroxyl group, or when taken together with $R_2$, may form an epoxy group; when $R_1$ means a hydroxyl group, $R_2$ is a halogen atom or a group of the formula —$OR_3$ (wherein $R_3$ is a p-toluenesulfonyl group, or an alkylsulfonyl group such as methanesulfonyl, ethanesulfonyl, propanesulfonyl or trifluoromethanesulfonyl group)]. This invention also relates to a compound of the formula (III):

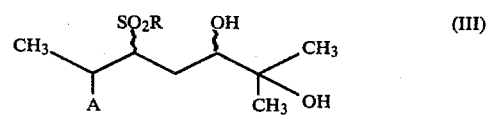

(wherein A and R are the same as defined above).

The compound (II) can be used in this invention in each of isomer (R,S-configuration) or racemic mixture at 24-position.

The steroid residue represented by A in the formulae (I) and (III) is a steroid bonded to 17-position, and specific examples are:

(a) 5,7-dienesteroids

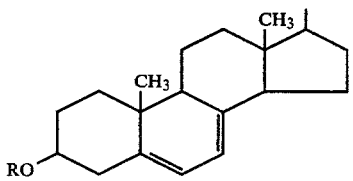

(wherein R is a protecting group for hydroxyl group);

(b) 3α,5-cyclosteroids

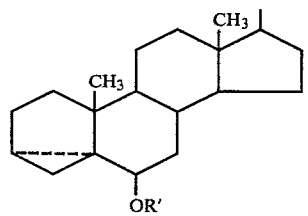

(wherein R' is a lower alkyl group, preferably a $C_1$-$C_3$ alkyl group) and (c) 5-ensteroids

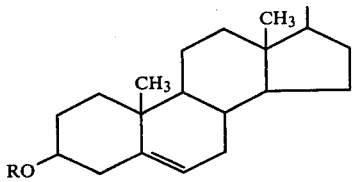

(wherein R is a protecting group for hydroxyl group).

The hydroxyl group at 3β-position of the steroids used as starting material for the practice of the process of this invention is preferably protected, and any protecting group that is inert to the reaction with the compound (II) can be used without particular limitation. The preferred protecting group is an ether group easy to remove by acid and stable to a base, and illustrative examples are 2-tetrahydropyranyl group, β-methoxyethoxymethyl group and methoxymethyl group. A lower alkylsilyl group such as dimethyl-t-butylsilyl is also a preferred protecting group. When 3β-hydroxy-5-ensteroids are used as the compound (I), the hydroxyl group at 3β-position is converted to tosylate, the 3-tosylate is refluxed in the presence of pyridine in an alcoholic solvent, preferably methanol, to obtain 6β-alkoxy-3α,5α-cyclosteroid as a protected form.

In the compound of the formula (I), A is the residual steroid described above, and R is a substituted or unsubstituted aryl group, for example a phenyl group or p-tolyl group. Examples of the compound (I) include 22-arylsulfonyl-23,24-bisnorchol-5-en-3β-ol or 22-arylsulfonyl-23,24-bisnor-5,7-choladien-3β-ol which has the hydroxyl group at 3β-position protected, and 20-arylsulfonylmethyl-6β-alkoxy-3α,5-cyclo-5α-pregnane.

These compounds are novel and can be prepared by the following methods:

(a) An ozone oxidation product (IV) of a 1,4-cyclic adduct of ergosterol 3-substituted derivative and 4-phenyl-1,2,4-triazoline-3,5-dione that is obtained from ergosterol by the method of Barton et al. [J.C.S. (c), 1971, 1968] is treated to give compound (Ia) via the following reaction scheme.

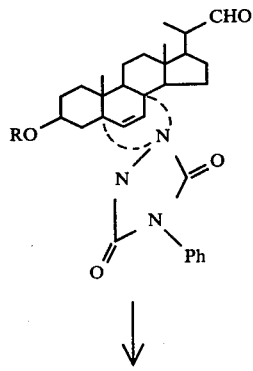
(IV)

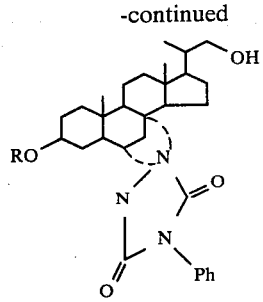
(V)

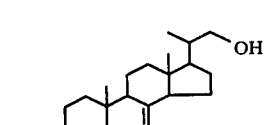
(VI)

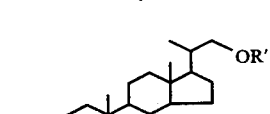
(VII)

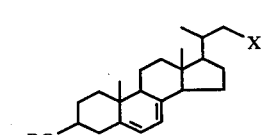
(VIII)

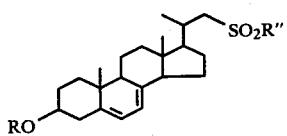
(Ia)

(wherein R is a protecting group for hydroxy group; R' is a p-toluenesulfonyl group, methanesulfonyl group and trifluoromethanesulfonyl group; X is a halogen atom; and R'' is a substituted or unsubstituted aryl group).

The reaction to convert the compound (IV) to (V) in the above scheme is performed by reduction with a conventional metal hydride such as sodium borohydride or lithium aluminum hydride. In the former reduction, the compound (V) is obtained as an intermediate and following reduction with lithium aluminum hydride gave the compound (VI). The latter with excess lithium aluminum hydride gave directly compound (VI). Reduction with lithium aluminum hydride is carried out usually in an aprotic organic solvent, such as tetrahydrofuran or diethyl ether. Then, the compound (VI) is converted to the compound (VII) by reaction with p-toluenesulfonyl chloride, methanesulfonyl chloride or trifluoromethanesulfonyl chloride in the presence of a base such as pyridine or triethyl-amine. Then, the compound (VII) is reacted with a metal halide such as NaBr or NaI in an aprotic polar solvent (e.g. acetone or acetonitrile) to give the halide compound (VIII). The halide compound (VIII) can also be obtained directly by treatment of the hydroxy compound (VI) with bromination agent such as 2-chloro-3-ethylbenzoxazolium tetrahydroborate and $Et_4NBr$, or with iodation agent such as a system containing triphenylphosphine and iodine in dimethylformamide. The compound (VIII) thus obtained is converted to the compound (Ia) by reaction with sodium arylsulfinate in an aprotic polar solvent such as dimethylformamide.

(b) 20-Halogenomethyl-6β-alkoxy-3α,5-cyclo-5α-pregnane obtained from stigmasterol by the method of Partridge et al [Helv. Chim. Acta., 57, 764 (1974)] is reacted with sodium arylsulfinate in an aprotic polar solvent such as dimethylformamide by the following the reaction scheme below:

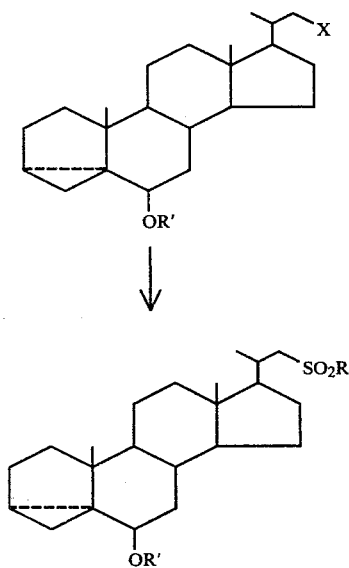

(Ib)

(wherein R is a substituted or unsubstituted aryl group; R' is a lower alkyl group; and X is a halogen atom).

The 22-arylsulfonyl-23,24-bisnorchol-5-en-3β-ol as compound (I) can be readily prepared by treatment of the compound (Ib) with acid and by subsequent introducing a protecting group into hydroxy group at 3β-position.

The reaction between the compound (I) and the compound (II) to produce the compound (III) is performed in a solvent in the presence of a base, and an inert solvent to the reaction may be used without particular limitation. The preferred solvent is an aprotic solvent, such as tetrahydrofuran, dimethoxyethane and diethyl ether. The preferred base is a strong base, for example, dialkyl metal amides such as lithium diisopropylamide, lithium cyclohexylisopropylamide, lithium 2,2,6,6-tetramethylpiperidide and lithium hexamethyldisilazane, and alkali metal alkyls such as t-butyl lithium. The reaction temperature is selected from the range of from −80° to 50° C. The reaction period is properly selected from the range of 10 minutes to 8 hours depending upon the reaction temperature, and preferably, the reaction is performed at between −70° and 0° C. for a period of 10 minutes to 1 hour. The compound (III) can be isolated from the reaction mixture by the conventional extraction method using an organic solvent such as ethyl acetate. The obtained crude compound (III) is purified by columnchromatography or other methods.

The 3-methyl-1,2,3-butanetriol derivative of the formula (II) is reacted with the compound (I) by nucleophilic attack introducing a 1-methyl-2,3-butanediol group into the side chain of the steroid residue. Illustrative examples are 3-methyl-1,2,3-butanetriol-1-tosylate, 3-methyl-1,2,3-butanetriol-1-mesylate, 2-(1-hydroxy-1-methyl-ethyl)oxyrane, and 1-halogen-3-methyl-2,3-butanediol. These compounds are novel, and in these novel compounds, the alkylsulfonate such as 1-tosylate or 1-mesylate can be obtained by reacting 3-methyl-1,2,3-butanetriol with a sulfonyl halide such as p-toluenesulfonyl chloride, methanesulfonyl chloride or trifluoromethanesulfonyl chloride in the presence of a basic material such as pyridine. 3-Methyl-1,2,3-butanetriol is easily prepared from an lower alkyl ester of glyceric acid and Grignard reagent (methyl magnesium halide) by the method of Nielsen et al [Acta. Chem. Scand., 23, 967 (1969)]. By treating the so produced alkyl sulfonate with a base, such as sodium hydride, potassium-t-butoxide or sodium methoxide, 2-(1-hydroxy-1-methyl-ethyl)oxyrane can be produced, and by treating the same alkyl sulfonate with an alkali metal halide such as lithium chloride or lithium bromide, 1-halogeno-3-methyl-2,3-butanediol can be produced. Each compound can be reacted with the compound (I) to give compound (III). Industrially advantageous reaction is direct treatment of alkylsulfonate with the compound (I) in the presence of a base to give compound (III), in which oxirane or 1-halogeno-compound is not separated as an intermediate. An optically active compound (II) can be prepared by using a lower alkyl ester of optically active glyceric acid as the starting material.

In the process of this invention, the absolute configuration of the compound (II) is retained in the compound (III). For instance, if an alkyl sulfonate of R-isomer of 3-methyl-1,2,3-butanetriol-1-tosylate or the like is reacted as compound (II) with the compound (I), an R-diastereomeric isomer at 24-position is obtained as compound (III), and if an S-isomer is used as compound (II), an S-diastereomeric isomer of the corresponding compound (III) is obtained respectively. In a similar manner, the use of a recemic mixture as compound (II) results in the production of a recemic mixture at 24-position of the compound (III).

The thus prepared compound (III) can be readily converted to a 24,25-dihydroxycholestane derivative (IX) by treating it with a reducing agent to remove the arylsulfonyl group at 22-position:

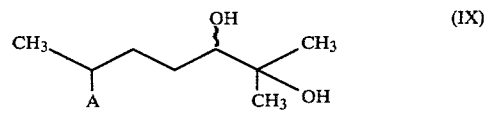

(IX)

(wherein A is a steroid residue as defined above).

The reducing agent used in the conversion of the compound (III) to (IX) may be used in any type that is capable of removal of arylsulfonyl group without affecting other functional groups. A preferred example of such reducing agent is a system comprising active metal amalgam and lower alcohol, specifically, a system comprising sodium amalgam or aluminum amalgam and lower alcohol. The content of active metal such as sodium or aluminum is preferably a few percent, and the preferred lower alcohol is methanol or ethanol. The reaction is preferably performed in a solvent inert to the reaction without particular limitation. The other solvent is not necessary if active metal amalgam and lower alcohol are used as reducing agent. The yield of reaction is increased by using disodium hydrogenphosphate or the like as a buffer. The reaction temperature is properly selected from the range of low temperatures to elevated temperatures. The compound (IX) can be easily isolated from the reaction mixture by a conventional method, for example, by extraction or recrystallization.

The absolute configuration at 24-position of the compound (III) is also retained in the compound (IX). The compound (IX) can be easily converted to 24,25-dihydroxycholecalciferol by the known method, for example, by the methods described in Tetrahedron Letters, 15 (1975), J.A.C.S., 98, 3739 (1976), and Japanese Patent Public Disclosure No. 108960/77. Again, the absolute configuration at 24-position of the compound (IX) are also retained even if it is subjected to these methods.

PREPARATION 1

(a) To a solution of 1.5 g of a 1,4-cyclic adduct of ergosterol 3-tetrahydropyranyl ether and 4-phenyl-1,2,4-triazoline-3,5-dione in 130 ml of dichloromethane and 80 ml of ethanol, ozone was passed through the solution under stirring at −78° C. until about 90% of the adduct was consumed. Then, a solution of 2.56 g of sodium borohydride in 20 ml of methanol was added to the reaction mixture which was stirred at −78° C. for 5 minutes followed by standing at room temperature for one hour. The reaction mixture was evaporated under reduced pressure, and the residue was dissolved in ethyl acetate, washed with saturated brine and dried over anhydrous sodium sulfate. The solvent was then evaporated and the residue was purified by columnchromatography using silicagel (150 g) and hexane:ethyl acetate (1:2) as an eluant to give 4.65 g (35%) of a 1,4-cyclic adduct of 23,24-bisnor-5,7-choladiene-3β,22-diol 3-tetrahydropyranyl ether and 4-phenyl-1,2,4-triazoline-3,5-dione.

m.p.: 192°-193° C. (recrystallized from hexane-ethyl acetate).

IR spectrum (KBr): 3470, 1750, 1700 cm$^{-1}$.

NMR spectrum (CDCl$_3$)δ: 0.83 (3 H,s), 0.97 (3 H,s), 1.06 (3 H,d,J=5 Hz), 4.85 (1 H,m), 6.25 (1 H,dd,J=8 and 2 Hz), 6.40 (1 H,d,J=8 Hz), 7.42 (5 H,m).

Mass spectrum m/e: 414

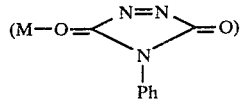

UV spectrum $\lambda_{max}^{EtOH}$: 255 nm.

Elemental analysis: Calculated for C$_{35}$H$_{47}$O$_5$N$_3$: C 71.28, H 8.03, N 7.13 (%). Found: C 70.99, H 8.06, N 7.02 (%).

(b) To a suspension of 634 mg of lithium aluminum hydride in 12 ml of tetrahydrofuran, a solution of 1.97 g of 1,4-cyclic adduct (as obtained in (a) above) in 25 ml of tetrahydrofuran was added dropwise with stirring under reflux in an argon stream for 10 minutes, and then, the mixture was left to stand for 15 minutes. A 20% aqueous solution (5 ml) of sodium hydroxide was carefully added dropwise to the reaction mixture at 0° C., and the precipitate was filtered. The filtrate was evaporated. The residue was purified by columnchromatography using silica gel (50 g) and hexane:ethyl acetate (5:3) as an eluant to give 879 mg (63%) of 23,24-bisnor-5,7-choladiene-3β,22-diol 3-tetrahydropyranyl ether.

m.p.: 151°-152° C. (recrystallized from hexane-ethyl acetate).

IR spectrum (KBr): 3380 cm$^{-1}$.

NMR spectrum (CDCl$_3$)δ: 0.63 (3 H,s), 0.94 (3 H,s), 1.09 (3 H,d,J=6 Hz), 4.75 (1 H,m), 5.39 (1 H,d,J=6 Hz), 5.58 (1 H,d,J=6 Hz).

Mass spectrum m/e: 414 (M+).

UV spectrum $\lambda_{max}^{EtOH}$: 272, 282, 294 nm.

Elemental analysis: Calculated for C$_{27}$H$_{42}$O$_3$: C 78.21, H 10.21 (%) Found: C 78.44, H, 10.43 (%).

(c) p-Toluenesulfonylchloride (199 mg) was added to a solution of 394 mg of 23,24-bisnor-5,7-choladiene-3β,22-diol 3-tetrahydropyranyl ether in a 4 ml of pyridine in an argon stream under stirring at 0° C., and the mixture was stirred overnight. To the reaction mixture ethyl acetate was added. The solution was washed first with saturated aqueous copper sulfate and then with saturated brine, and drive over anhydrous sodium sulfate. The solvent was evaporated under reduced pressure the residue was purified by column-chromatography using silica gel (5 g) and methylene chloride as an eluant to give 432 mg (80%) of 23,24-bisnor-5,7-choladiene-3β,22-diol 3-tetrahydropyranyl ether-22-tosylate (yield:80%).

m.p.: 147°-149° C. (recrystallized from hexane-ethyl acetate).

IR spectrum (KBr): 1350, 1170 cm$^{-1}$.

NMR spectrum (CDCl$_3$)δ: 0.58 (3 H,s), 0.93 (3 H,s), 1.00 (3 H,d,J=6 Hz), 4.73 (1 H,m), 5.36 (1 H,d,J=5 Hz), 5.54 (1 H,d,J=5 Hz), 7.35 (2 H,d,J=8 Hz), 7.78 (2 H,d,J=8 Hz).

Mass spectrum m/e: 484

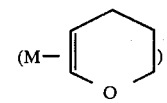

UV spectrum $\lambda_{max}^{EtOH}$: 272, 282, 294 nm.

Elemental analysis: Calculated for C$_{34}$H$_{48}$O$_5$S: C 71.78, H 8.51 (%). Found: C 71.66, H 8.61 (%).

(d) A mixture of 100 mg of 23,24-bisnor-5,7-choladiene-3β,22-diol 3-tetrahydropyranyl ether-22-tosylate, 37 mg of lithium bromide monohydrate, 26 mg of lithium carbonate in 3 ml of dimethylformamide was stirred for one hour in an argon stream at 75° C. The reaction mixture was extracted with ethyl acetate. The organic layer was washed with saturated brine and dried over anhydrous sodium sulfate. The solvent was evaporated under reduced pressure to give 82 mg (98%) of 22-bromo-23,24-bisnor-5,7-choladiene-3-ol-3-tetrahydropyranyl ether.

m.p.: 150°-152° C. (recrystallized from hexane)

NMR spectrum (CDCl$_3$)δ: 0.65 (3 H,s), 0.95 (3 H,s), 1.13 (3 H,d,J=6 Hz), 4.72 (1 H,m), 5.37 (1 H,d,J=5 Hz), 5.55 (1 H,d,J=5 Hz).
Mass spectrum m/e: 478, 476 (M+).
UV spectrum $\lambda_{max}^{EtOH}$: 272, 282, 294 nm.
Elemental analysis: Calculated for C$_{27}$H$_{41}$O$_2$Br: C 67.91, H 8.65 (%). Found: C 67.66, H 8.71 (%).

(e) A mixture of 60 mg of 22-bromo-23,24-bisnor-5,7-choladiene-3β-ol 3-tetrahydropyranyl ether, 52 mg of sodium benzenesulfinate in 1 ml of dimethylformamide was stirred for one hour at 75° C. in an argon stream. To the reaction mixture ethyl acetate was added. The organic layer was washed with saturated brine and dried over anhydrous sodium sulfate. The solvent was evaporated under reduced pressure and the residue was purified by columnchromatography using silica gel (10 g) and hexane:ethyl acetate (10:3) as an eluant to give 53 mg of 22-phenylsulfonyl-23,24-bisnor-5,7-choladiene-3β-ol 3-tetrahydropyranyl ether.
m.p.: 175°–177° C. (recrystallized from ethyl acetate).
IR spectrum (KBr): 1295, 1135 cm$^{-1}$.
NMR spectrum (CDCl$_3$)δ: 0.59 (3 H,s), 0.92 (3 H,s), 1.23 (3 H,d,J=6 Hz), 4.74 (1 H,m), 5.35 (1 H,d,J=5 Hz), 5.54 (1 H,d,J=5 Hz), 7.5–8.0 (5 H,m).
Mass spectrum m/e: 538 M+).
UV spectrum $\lambda_{max}^{EtOH}$: 271, 282, 294 nm.

PREPARATION 2

(a) Pyridinium p-toluenesulfonate (50 mg) was added to a solution of 8.3 g of (R)-methyl glycerate in 30 ml of 2,2-dimethoxypropane and the mixture was refluxed for 30 minutes. The reaction mixture was purified by columnchromatography using silica gel (120 g) and hexane:ethyl acetate (5:1) as an eluant to give 9.87 g (89%) of (R)-methyl glycerate acetonide.
NMR spectrum (CDCl$_3$)δ: 1.41 (3 H,s), 1.50 (3 H,s), 3.80 (3 H,s), 4.0–4.7 (3 H,m).

(b) A solution of 1.126 g of (R)-methyl glycerate acetonide in tetrahydrofuran was added dropwise to a solution of methyl magnesium bromide in tetrahydrofuran (1 mol/l, 21 ml) under stirring in an argon stream at 0° C., and the mixture was stirred for 30 minutes. A saturated ammonium chloride solution (2.1 ml) was added to the reaction mixture. The precipitate was filtered and the filtrate was evaporated under reduced pressure and the residue was purified by columnchromatography using silica gel (50 g) and hexane:ethyl acetate (5:2) as an eluant to give 841 mg (75%) of (R)-3-methyl-1,2,3-butanetriol acetonide.
NMR spectrum (CDCl$_3$)δ: 1.14 (3 H,s), 1.24 (3 H,s), 1.37 (3 H,s), 1.44 (3 H,s), 2.12 (1 H,s), 3.8–4.3 (3 H,m).
[α]$_D$= +5.03° (C=2.88, CH$_3$OH).

(c) Pyridinium p-toluenesulfonate (304 mg) was added to a solution of 1.94 g of (R)-3-methyl-1,2,3-butanetriol acetonide in 20 ml of 20% aqueous methanol, and the mixture was refluxed for 3 hours. The reaction mixture was evaporated under reduced pressure, and then benzene and ethanol were added to the residue and water was removed completely by azeotropic distillation. The residue was purified by columnchromatography using silica gel (50 g) ethyl acetate:ethanol (20:1) as an eluant to give 1.381 g (95%) of (R)-3-methyl-1,2,3-butanetriol.
NMR spectrum (CDCl$_3$)δ: 1.20 (3 H,s), 1.25 (3 H,s), 3.4–4.7 (6 H,m).
[α]$_D$= +23.85° C. (C=0.96, CH$_3$OH).

(d) p-Toluenesulfonylchloride (4.03 g) was added to a solution of 2.52 g of (R)-3-methyl-1,2,3-butanetriol in 15 ml of pyridine under stirring in an argon stream at 0° C., and the mixture was stirred at 0° C. for one hour, and at room temperature for 16 hours. The reaction mixture was poured into 100 ml of 2 N hydrochloric acid and extracted with ethyl acetate. The organic layer was washed with 2 N hydrochloric acid, saturated sodium hydrogencarbonate and saturated brine, and dried over anhydrous sodium sulfate. The solvent was evaporated to give 4.70 g (85%) of (R)-3-methyl-butanetriol-1-tosylate.
m.p.: 103°–104° C. (recrystallized from benzene).
IR spectrum (KBr): 3330, 1350, 1190, 1170 cm$^{-1}$.
NMR spectrum (CDCl$_3$)δ: 1.16 (3 H,s), 1.21 (3 H,s), 2.15 (1 H,s), 2.45 (3 H,s), 2.80 (1 H,d,J=4 Hz), 3.70 (1 H,m), 3.9–4.4 (2 H,m), 7.39 (1 H,d,J=8 Hz), 7.82 (1 H,d,J=8 Hz).
UV spectrum $\lambda_{max}^{EtOH}$: 256, 263, 266, 273 nm.
[α]$_D$= +32.1° C. (C=0.448, CH$_3$OH).
Elemental analysis: Calculated for C$_{12}$H$_{18}$O$_5$S: C 52.54, H 6.61 (%), Found: C 52.80, H 6.67 (%).

PREPARATION 3

(a) A mixture of 1 g of anhydrous disodium hydrogenephosphate and 3.2 g of 5% sodium-amalgam was added to a solution of 160 mg of (24R)-22ξ-phenylsulfonyl-5,7-cholestadiene-3β,24,25-triol 3-tetrahydropyranyl ether in 5 ml of methanol in an argon stream under stirring, and the mixture was stirred for 30 minutes at room temperature. To the reaction mixture 10 ml of methanol was added and the precipitate was filtered. The filtrate was evaporated under reduced pressure and the residue was extracted with ethyl acetate. The organic layer was washed with saturated brine and dried over anhydous sodium sulfate. The solvent was evaporated under reduced pressure to give 11.6 mg (93%) of (24R)-5,7-cholestadiene-3β,24,25-triol 3-tetrahydropyranyl ether.
m.p.: 149°–150° C. (recrystallized from hexane-dimethoxyethane).
IR spectrum (CHCl$_3$): 3580, 3440 cm$^{-1}$.
NMR spectrum (CDCl$_3$)δ: 0.64 (3 H,s), 0.95 (3 H,s), 1.18 (3 H,s), 1.22 (3 H,s), 4.76 (1 H,m), 5.40 (1 H,d,J=5 Hz), 5.58 (1 H,d,J=5 Hz).
Mass spectrum m/e: 500 (M+).
UV spectrum $\lambda_{max}^{EtOH}$: 272, 282, 294 nm.

(b) Pyridinium p-toluenesulfonate (12.5 mg) was added to a solution of (24R)-5,7-cholestadiene-3β,24,25-triol 3-tetrahydropyranyl ether (25 mg) in 2 ml of ethanol in an argon stream under stirring, and the mixture was left to stand at room temperature for 2 days. The reaction mixture was evaporated with 40 ml of ethyl acetate. The organic layer was washed with saturated brine and dried over anhydrous sodium sulfate. The solvent was evaporated under reduced pressure to give 14 mg (67%) of (24R)-5,7-cholestadiene-3β,24,25-triol.
m.p.: 216°–218° C. (recrystallized from ethyl acetate)

NMR spectrum (CDCl$_3$, CD$_3$OD)δ: 0.64 (3 H,s), 0.94 (3 H,s), 1.15 (3 H,s), 1.19 (3 H,s), 3.3–3.8 (2 H,m), 5.38 (1 H,d,J=5 Hz), 5.56 (1 H,d,J=5 Hz).

Mass spectrum m/e: 416 (M+).

UV spectrum λ$_{max}$$^{EtOH}$: 272, 282, 294 nm.

(c) A solution of 12.1 mg of (24R)-5,7-cholestadiene-3β,24,25-triol in 20 ml of ethanol was diluted with 200 ml of ether. The solution was irradiated under argon atmosphere with high-pressure mercury lamp (200 W) through a Vycor filter for 4.5 minutes. The reaction mixture was evaporated under reduced pressure on a water bath below 20° C. The residue was purifieed by chromatography using Sephadex LH-20 (20 g) and CHCl$_3$:hexane (65:35) as an eluant to give 4.53 mg of (24R)-9,10-seco-5(10),6,8-cholestatriene-3β,24,25-triol.

(d) A solution of 4.53 mg of (24R)-9,10-seco-5(10),6,8-cholestatriene-3β,24,25-triol in 15 ml of ethanol was refluxed at 2 hours in an argon stream and left to stand for 24 hours at room temperature. The reaction mixture was evaporated under reduced pressure below 20° C., and the residue was purified by high speed liquid chromatography using μ-porasil (Waters Corp) as a solid phase and a hexane:isopropanol (10:1) as a mobile phase. Evaporation of eluate gave 1.85 mg of (24R)-24,25-dihydroxycholecalciferol was obtained.

NMR spectrum (CDCl$_3$)δ: 0.55 (3 H,s), 0.93 (3 H,d,J=4 Hz), 1.17 (3 H,s), 1.22 (3 H,s), 3.33 (1 H,m), 3.95 (1 H,m), 4.85 (1 H,bs), 5.07 (1 H,bs), 6.08 (1 H,d,J=11 Hz), 6.25 (1 H,d,J=11 Hz).

Mass spectrum m/e: 416 (M+), 136, 118.

UV spectrum λ$_{max}$$^{EtOH}$: 265 nm.

EXAMPLE 1

A solution of n-butyl lithium in hexane (1.53 mol/l, 670 μl) was added dropwise to a solution of 100 mg of 22-phenylsulfonyl-23,24-bis-nor-5,7-choladiene-3β-ol 3-tetrahydropyranyl ether and 100 mg of (R)-3-methyl-1,2,3-butanetriol 1-tosylate in 2 ml of tetrahydrofuran in an argon stream at −20° C. under stirring, and the mixture was left to stand for 30 minutes. The reaction liquor was poured into a saturated solution of ammonium chloride and extracted with ethyl acetate. The organic layer was washed with a saturated solution of ammonium chloride and saturated brine, and dried over anhydrous sodium sulfate. The solvent was evaporated under reduced pressure and the resulting residue was purified by columnchromatography using silica gel (20 g) and hexane:ethyl acetate (1:1) as an eluent to give 102 mg (86%) of (24R)-22ξ-phenylsulfonyl-5,7-cholestadiene-3β,24,25-triol 3-tetrahydropyranyl ether.

IR spectrum (CHCl$_3$): 1300, 1135 cm$^{-1}$.

NMR spectrum (CDCl$_3$)δ: 4.72 (1 H,m), 5.32 (1 H,d,J=5 Hz), 5.52 (1 H,d,J=5 Hz), 7.4–8.0 (5 H,m)

Mass spectrum m/e: 640 (M+).

UV spectrum λ$_{max}$$^{EtOH}$: 271, 282, 294 nm.

What is claimed is:

1. A 24,25-dihydroxycholestane derivative of the formula:

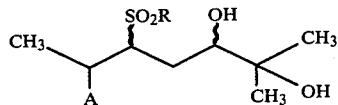

(wherein A is a steroid residue of one of the following formulas (a), (b) and (c), and R is an aryl group)

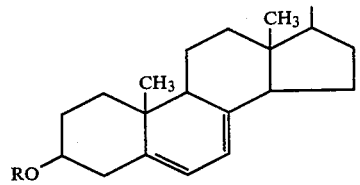

(wherein R is a protecting group for hydroxyl group);

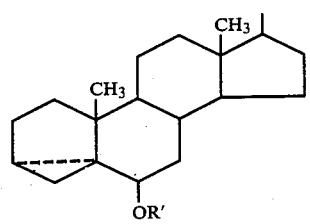

(wherein R' is a lower alkyl group); and

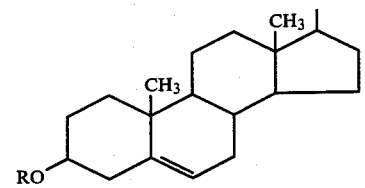

(wherein R is a protecting group for hydroxyl group).

2. A 22-arylsulfonyl-5,7-cholestadiene-3β,24,25-triol derivative of the formula:

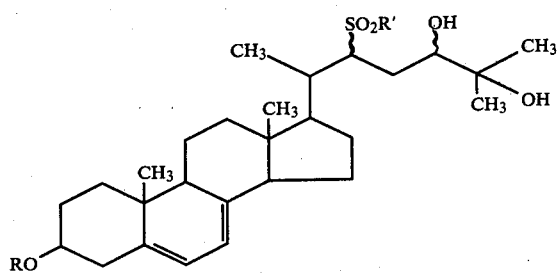

(wherein R is a tetrahydropyranyl group, β-methoxyethoxymethyl group, methoxymethyl group or t-butyldimethylsilyl group, and R' is a phenyl group or monosubstituted phenyl group).

3. A 22-phenylsulfonyl-5,7-cholestadiene-3β,24,25-triol 3-tetrahydropyranyl ether according to claim 1.

4. A process for producing a 24,25-dihydroxycholestane derivative of the formula:

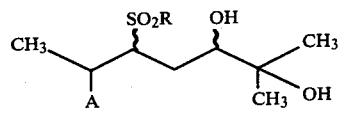

(wherein A is a steroid residue of one of the following formulas (a), (b) and (c), and R is an aryl group)

(a)

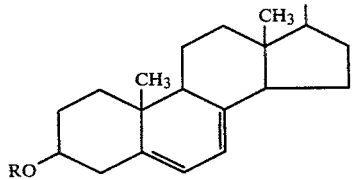

(wherein R is a protecting group for hydroxyl group);

(b)

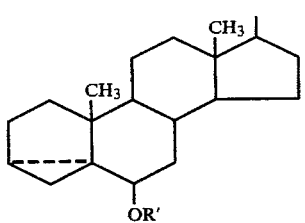

(wherein R' is a lower alkyl group); and

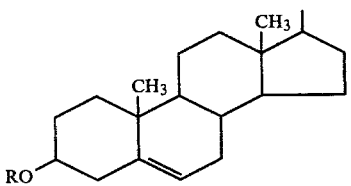

(wherein R is a protecting group for hydroxyl group) which comprises reacting a compound of the formula:

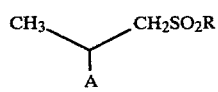

(wherein A and R are the same as defined above) with a compound of the formula:

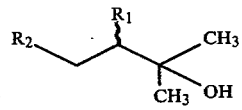

5. A process according to claim 4 wherein the reaction is performed in an aprotic solvent such as tetrahydrofuran, dimethoxyethane or diethyl ether in the presence of a base.

6. A process according to claim 5 wherein the base is an alkali metal amide such as lithium diisopropylamide, lithium cyclohexylisopropylamide, lithium 2,2,6,6-tetramethylpiperidide or lithium hexamethyldisilazane, or an alkali metal alkyl such as t-butyl lithium.

7. A process according to claim 4 wherein the reaction is performed at a temperature between $-80°$ C. and $50°$ C. for a period of 10 minutes to 8 hours.

8. A process according to claim 4 wherein the reaction is performed at a temperature between $-70°$ C. and $0°$ C. for a period of 10 minutes to 1 hour.

* * * * *

UNITED STATES PATENT AND TRADEMARK OFFICE
CERTIFICATE OF CORRECTION

PATENT NO. : 4,344,888
DATED : August 17, 1982
INVENTOR(S) : TAKAYAMA et al

It is certified that error appears in the above-identified patent and that said Letters Patent are hereby corrected as shown below:

Column 3, structural formula (IV) should read as follows:

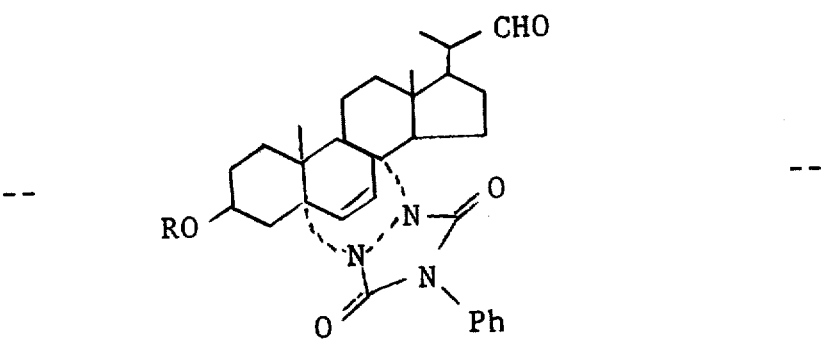

-- --

Column 4, structural formula (V) should read as follows:

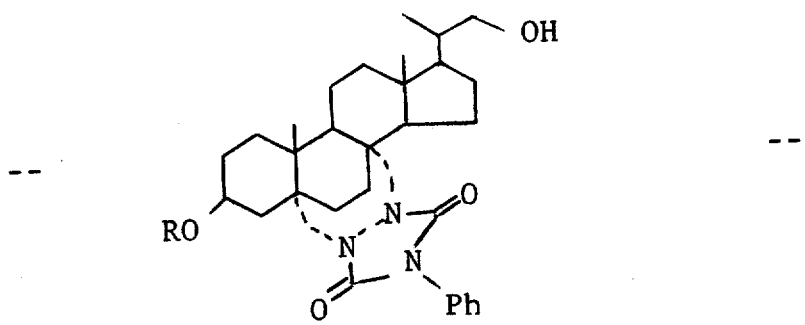

-- --

UNITED STATES PATENT AND TRADEMARK OFFICE
CERTIFICATE OF CORRECTION

PATENT NO. : 4,344,888

DATED : August 17, 1982

INVENTOR(S) : TAKAYAMA et al

It is certified that error appears in the above-identified patent and that said Letters Patent are hereby corrected as shown below:

Column 12, Claim 3, line 1, that portion of the formula reading "-3β24,25-" should read:

Signed and Sealed this

Twenty-first Day of June 1983

[SEAL]

Attest:

DONALD J. QUIGG

Attesting Officer

Acting Commissioner of Patents and Trademarks